(12) United States Patent
Barth et al.

(10) Patent No.: US 9,504,381 B2
(45) Date of Patent: *Nov. 29, 2016

(54) SYSTEM AND METHOD FOR THE NON-CONTACTING MEASUREMENTS OF THE EYE

(71) Applicant: Carl Zeiss Meditec AG, Jena (DE)

(72) Inventors: Roland Barth, Jena (DE); Roland Bergner, Jena (DE); Lothar Mueller, Ottendorf (DE); Dietmar Steinmetz, Bucha (DE); Siegfried Schubert, Jena (DE); Klaus-Ditmar Voigt, Jena (DE); Frank Behrendt, Jena (DE); Burkhard Dietzel, Buergel (DE); Axel Doering, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/318,022

(22) Filed: Jun. 27, 2014

(65) Prior Publication Data
US 2014/0375951 A1 Dec. 25, 2014

Related U.S. Application Data

(63) Continuation of application No. 13/445,669, filed on Apr. 12, 2012, now Pat. No. 8,764,195, which is a
(Continued)

(30) Foreign Application Priority Data

Dec. 10, 1998 (DE) .................. 198 570 007
Dec. 10, 1998 (DE) .................. 198 570 015

(51) Int. Cl.
*A61B 3/00* (2006.01)
*A61B 3/10* (2006.01)
(Continued)

(52) U.S. Cl.
CPC .......... *A61B 3/1005* (2013.01); *A61B 3/0008* (2013.01); *A61B 3/0025* (2013.01); *A61B 3/107* (2013.01); *A61B 3/117* (2013.01); *A61B 3/14* (2013.01); *A61B 8/10* (2013.01)

(58) Field of Classification Search
CPC .... A61B 3/1005; A61B 3/0025; A61B 3/14; A61B 3/0008; A61B 3/107; A61B 3/117; A61B 8/10
See application file for complete search history.

(56) References Cited

U.S. PATENT DOCUMENTS 3,785,723 A 1/1974 Guyton
4,019,813 A 4/1977 Cornsweet et al.
(Continued)

FOREIGN PATENT DOCUMENTS

DE 2 51 497 10/1912
DE 31 50 124 A1 7/1983
(Continued)

OTHER PUBLICATIONS

J. Cataract Refract Surg. vol. 35. Nov. 1997 (pp. 1351-1355); Measuring Anterior Chamber Depth With the Orbscan Topography System; Auffarth et al.
(Continued)

*Primary Examiner* — Jordan Schwartz
(74) *Attorney, Agent, or Firm* — Patterson Thuente Pedersen, P.A.

(57) ABSTRACT

Combined equipment for non-contacting determination of axial length (AL), anterior chamber depth (VKT) and corneal curvature (HHK) of the eye, are also important for the selection of the intraocular lens IOL to be implanted, particularly the selection of an intraocular lens (IOL) to be implanted, preferably with fixation of the eye by means of a fixating lamp and/or illumination through light sources grouped eccentrically about the observation axis.

15 Claims, 9 Drawing Sheets

Related U.S. Application Data continuation of application No. 11/932,170, filed on Oct. 31, 2007, now abandoned, which is a continuation of application No. 10/916,151, filed on Aug. 10, 2004, now Pat. No. 7,322,699, which is a continuation of application No. 09/857,599, filed as application No. PCT/EP99/09766 on Dec. 10, 1999, now Pat. No. 6,779,891.

(51) Int. Cl.
*A61B 3/117* (2006.01)
*A61B 3/107* (2006.01)
*A61B 3/14* (2006.01)
*A61B 8/10* (2006.01)

(56) References Cited

U.S. PATENT DOCUMENTS

| | | | |
|---|---|---|---|
| 4,420,228 A | 12/1983 | Humphrey | |
| 4,523,821 A | 6/1985 | Lang et al. | |
| 4,533,221 A | 8/1985 | Trachtman | |
| 4,572,628 A | 2/1986 | Nohda | |
| 4,582,404 A | 4/1986 | Hamilton | |
| 4,660,946 A | 4/1987 | Nakamura et al. | |
| 4,711,541 A | 12/1987 | Yoshino et al. | |
| 4,764,006 A | 8/1988 | Hamano et al. | |
| 4,930,512 A | 6/1990 | Henriksen et al. | |
| 5,042,938 A | 8/1991 | Shimozono | |
| 5,092,880 A | 3/1992 | Ohmi | |
| 5,094,521 A | 3/1992 | Jolson et al. | |
| 5,139,022 A | 8/1992 | Lempert | |
| 5,212,507 A | 5/1993 | Fujieda et al. | |
| 5,280,313 A | 1/1994 | Kohayakawa | |
| 5,282,852 A | 2/1994 | Capetan et al. | |
| 5,325,134 A | 6/1994 | Kohayakawa | |
| 5,325,135 A | 6/1994 | Nakamura et al. | |
| 5,331,962 A | 7/1994 | Coleman et al. | |
| 5,347,327 A * | 9/1994 | Sekine | A61B 3/1005 351/205 |
| 5,349,399 A * | 9/1994 | Sekine | A61B 3/1005 351/211 |
| 5,386,258 A | 1/1995 | Niagano | |
| 5,416,538 A | 5/1995 | Yamada | |
| 5,432,596 A | 7/1995 | Hayashi | |
| 5,463,430 A | 10/1995 | Isogai et al. | |
| 5,491,524 A | 2/1996 | Hellmuth et al. | |
| 5,493,109 A | 2/1996 | Wei et al. | |
| 5,512,965 A | 4/1996 | Snook | |
| 5,563,667 A | 10/1996 | Isogai et al. | |
| 5,673,096 A | 9/1997 | Dorsei et al. | |
| 5,735,283 A | 4/1998 | Snook | |
| 5,745,176 A | 4/1998 | Lebens | |
| 5,757,462 A | 5/1998 | Nanjo | |
| 5,784,146 A | 7/1998 | Nanjo et al. | |
| 5,828,489 A | 10/1998 | Johnson et al. | |
| 6,079,831 A | 6/2000 | Sarver et al. | |
| 6,095,648 A * | 8/2000 | Birngruber | A61B 3/1225 351/214 |
| 6,331,062 B1 | 12/2001 | Sinclair | |
| 6,404,984 B1 | 6/2002 | Parvulescu et al. | |
| 6,779,891 B1 | 8/2004 | Barth et al. | |
| 2004/0061830 A1* | 4/2004 | Hellmuth | A61B 3/1005 351/205 |

FOREIGN PATENT DOCUMENTS

| | | |
|---|---|---|
| DE | 3 201 801 | 9/1983 |
| DE | 251 497 A1 | 11/1987 |
| DE | 44 46 183 | 6/1996 |
| EP | 0 563 454 | 12/1992 |
| EP | 0 811 352 | 6/1994 |
| EP | 0 776 628 A2 | 6/1997 |

OTHER PUBLICATIONS

Arch Opthalmol. vol. 112. Dec. 1994 (pp. 1584-1587); Micrometer-Scale Resolution Imaging of the Anterior Eye in Vivo With Optical Coherence Tomography; Izatt et al.

Ophthalmic Res. 1992; 24 (Suppl. 1) (pp. 10-20); Reproductibility of Data Obtained by a Newly Developed Anterior Eye Segment Analysis System EAS-1000; Sakamoto et al.

Lasers in Surgery and Medicine; U.S. Wileyliss, New York; vol. 13, No. 4; Jan. 1993 (pp. 447-452); Slit Lamp Laser Doppler Interferometer; Fercher et al.

German Search Report for German Application No. 99963480.1-2217 dated Sep. 10, 2010.

Knorz et al., "Automatische Biometrie and Keratometrie im Vergleich zur manuellen Technik", Fortschr Ophthalmol (1989); 86:157-158 and English language Abstract.

Application and File History of U.S. Appl. No. 10/916,151, filed Aug. 10, 2004. Inventors: Barth et al.

Application and File History of U.S. Appl. No. 11/932,170, filed Oct. 31, 2007. Inventors: Barth et al.

Application and File History of U.S. Appl. No. 13/445,669, filed Apr. 12, 2012. Inventors: Barth et al.

* cited by examiner

SYSTEM AND METHOD FOR THE NON-CONTACTING MEASUREMENTS OF THE EYE

RELATED APPLICATIONS

This application is a continuation of application Ser. No. 13/445,669 filed Apr. 12, 2012 which is a continuation of application Ser. No. 11/932,170 filed Oct. 31, 2007, which in turn is a continuation of application Ser. No. 10/916,151 filed Aug. 10, 2004, now U.S. Pat. No. 7,322,699 issued Jan. 29, 2008, which is a continuation of U.S. application Ser. No. 09/857,599, filed Jun. 7, 2001, now U.S. Pat. No. 6,779,891 issued Aug. 24, 2004, which claims priority to DE 1985 70007, filed Dec. 10, 1998, DE 1985 70015, filed Dec. 10, 1998 and PCT/EP 99/09766, filed Dec. 10, 1999 each of which is hereby incorporated herein in its entirety by reference.

BACKGROUND OF THE INVENTION

Figure 1:
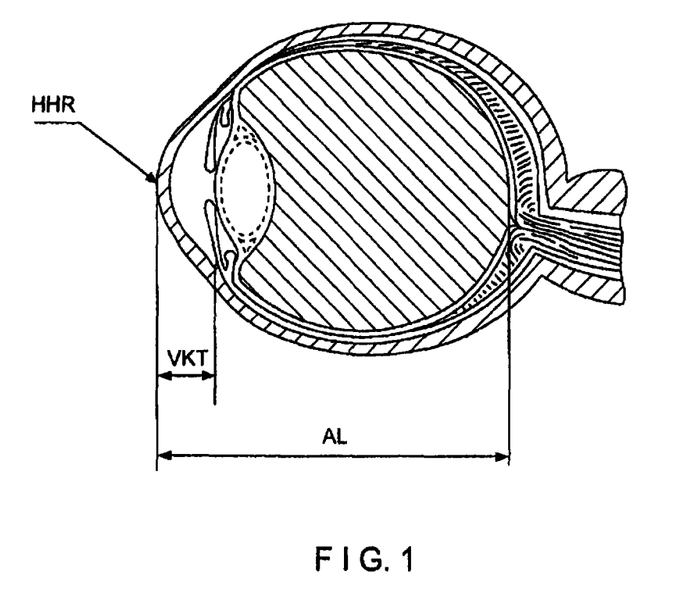
FIG. 1 schematically shows a longitudinal section through the human eye.

A longitudinal section through the human eye is shown schematically in FIG. 1. The axial length AL of the human eye is usually measured by a contact ultrasound method. Other measuring methods are described in DE 3201801, U.S. Pat. No. 5,673,096 and DE 4446183 A1. The curvature of the cornea-cornea radius HHR is determined by means of known keratometers/opthalmometers (DD 251497, U.S. Pat. Nos. 4,572,628, 4,660,946, 5,212,507 and 5,325,134). The measurement of the anterior chamber depth VKT can be carried out by ultrasound or by means of a unit added to a slit lamp (anterior chamber depth gauge, adjustment via the slit lamp image).

These measurements, which are also important for selecting the intraocular lens IOL to be implanted, must be determined particularly before a cataract operation, but also to monitor the progress of school children's myopia and to detect aniseikonia. In clinical practice, it is common to measure these quantities by means of at least two devices (e.g. ultrasonic a-scan and automatic keratometer). The measured quantities are used in formulas for calculating the optical power of the IOL. Various errors influencing the choice of IOL can occur depending on the type of device used.

SUMMARY OF THE INVENTION

It is the primary object of the invention to reduce these device-dependent measurement errors to a minimum.

In accordance with the invention, a combination device for non-contacting measurement of axial length and corneal curvature of an eye comprises an interferometer arrangement with adjustable path length difference, a first splitter cube which images the radiation of the interferometer arrangement on the eye, a photo-diode on which partial beams reflected during axial length measurement at the cornea and retina are coupled out via a second splitter cube and a focusing element, a plurality of light sources which are arranged concentric and symmetric to the optical axis of the eye and which illuminate the eye diagonal to the optical axis with a punctiform image for measurement of corneal curvature, and a camera on which the reflections of punctiform images of the light sources occurring at the cornea during measurement of corneal curvature are imaged via the first and the second splitter cubes, wherein a part of the radiation from the interferometer arrangement that is reflected on the cornea and retina is imaged on the camera for purposes of observation.

The invention also encompasses a method for determining the corneal curvature radius and/or the anterior chamber of a human eye.

According to the invention, all necessary parameters of the eye are advantageously determined by means of a device arrangement and corresponding measurement methods.

Necessary adjustments which make it possible to adjust the device to the patient are likewise realized in this arrangement.

The calculation of the IOL is also carried out by means of this device arrangement. Accordingly, there is also no lost or corrupted data in the transmission of measurements from various devices to the computer carrying out the IOL calculation. The invention and its advantages are described in more detail in the following with reference to schematic drawings.

DETAILED DESCRIPTION OF THE DRAWINGS

Figure 2:
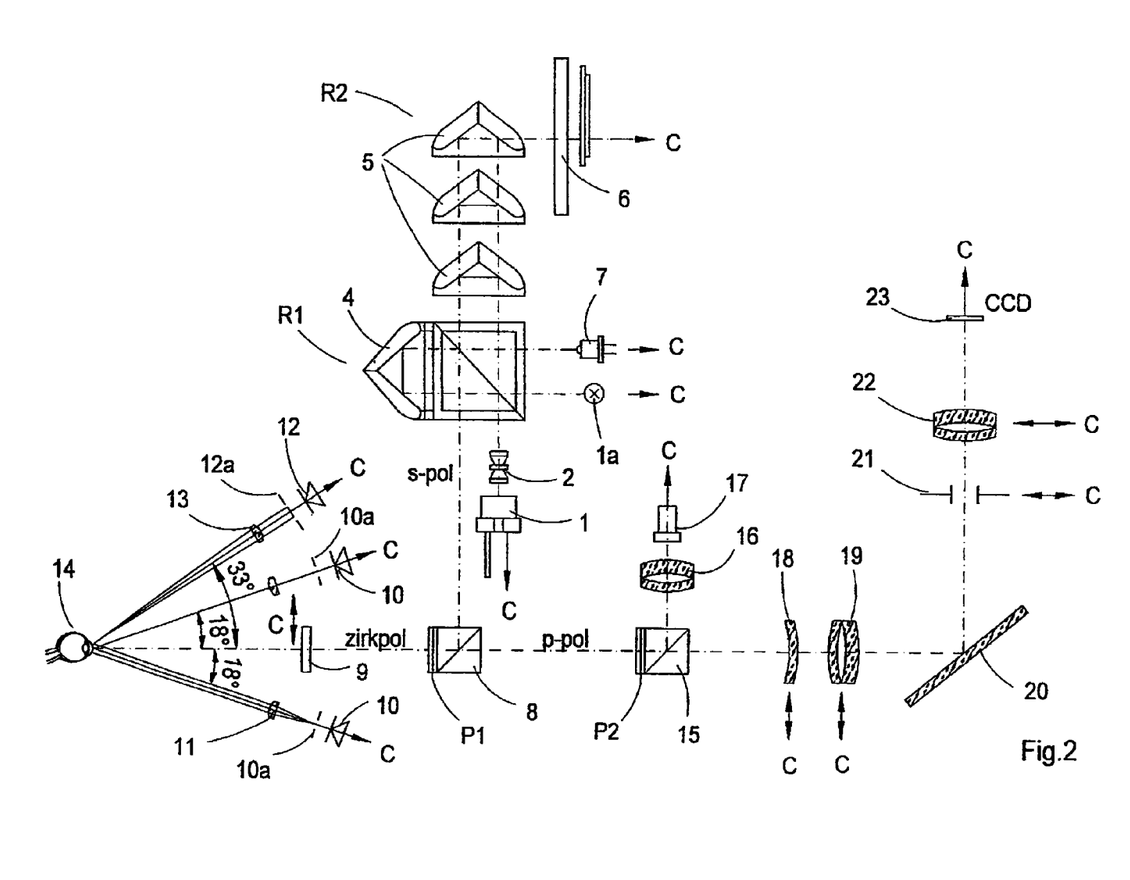
FIG. 2 schematically illustrates the construction of the overall device.

The construction of the device is shown schematically in FIG. 2. In order to measure axial length, the light of a laser diode 1 is imaged on the patient's eye 14 via a Michelson interferometer (3-5) comprising a stationary reference arm R1 with a reflector 4, in this case a triple prism, and an adjustable reference arm R2 shown with reference to different positions of another reflector 5 (triple prism), as well as a beam splitter cube 3 for superposition of the beam components reflected in R1 and R2, a splitter cube 8, and a diffractive-optical element DOE 9. A diode 7 monitors the light output of the laser diode 1. The partial beams reflected by the cornea and retina of the eye 14 are superposed on one another and are imaged, via a focusing element, in this case an achromate 16, on an avalanche photodiode APD 17 by means of DOE 9, splitter cube 8 having a quarter-wave plate P1 for rotation of the polarization plane, and splitter cube 15 with a half-wave plate P2. In this connection, the axial length is measured according to known methods which are described, for example, in U.S. Pat. No. 5,673,096.

In order to observe the eye and the occurring reflections, a portion of the reflected light (light coming from the eye) is imaged on a CCD camera 23 by means of an achromate 22 via mirror 20. Achromates 18, 19 are swiveled out in this case. In this connection, a diaphragm 21 is in the off setting.

In order to measure the corneal curvature HHK, the eye 14 is illuminated in a manner analogous to DD 251497 at an angle of approximately 18.degree. to the optical axis A1 by means of six, preferably infrared, LEDs 10, two of which are shown by way of example in the drawing plane in FIG. 1. Pinhole diaphragms 10a are arranged downstream of the LEDs to generate punctiform illumination images.

Six lenses 11 are arranged downstream of the LEDs in the illumination direction for collimating the diode light. The images of these light sources formed in the eye (as reflection of the cornea) are imaged on the CCD camera via splitter cubes 8 and 15 and achromates 18 and 19. The DOE 9 is advantageously swiveled out, but can also remain in the beam path. The achromate 22 is swiveled out.

Each eye is illuminated slitwise at an angle of approximately 33.degree. by means of LED 12, slide diaphragm 12a and cylindrical lens 13 in order to determine the VKT. The resulting scatter images of the cornea and front lens surface are imaged on the CCD camera 23 via splitter cubes 8 and 15 and achromates 18 and 19 with the DOE preferably being swiveled out. The achromate 22 is swiveled out.

Figure 3:
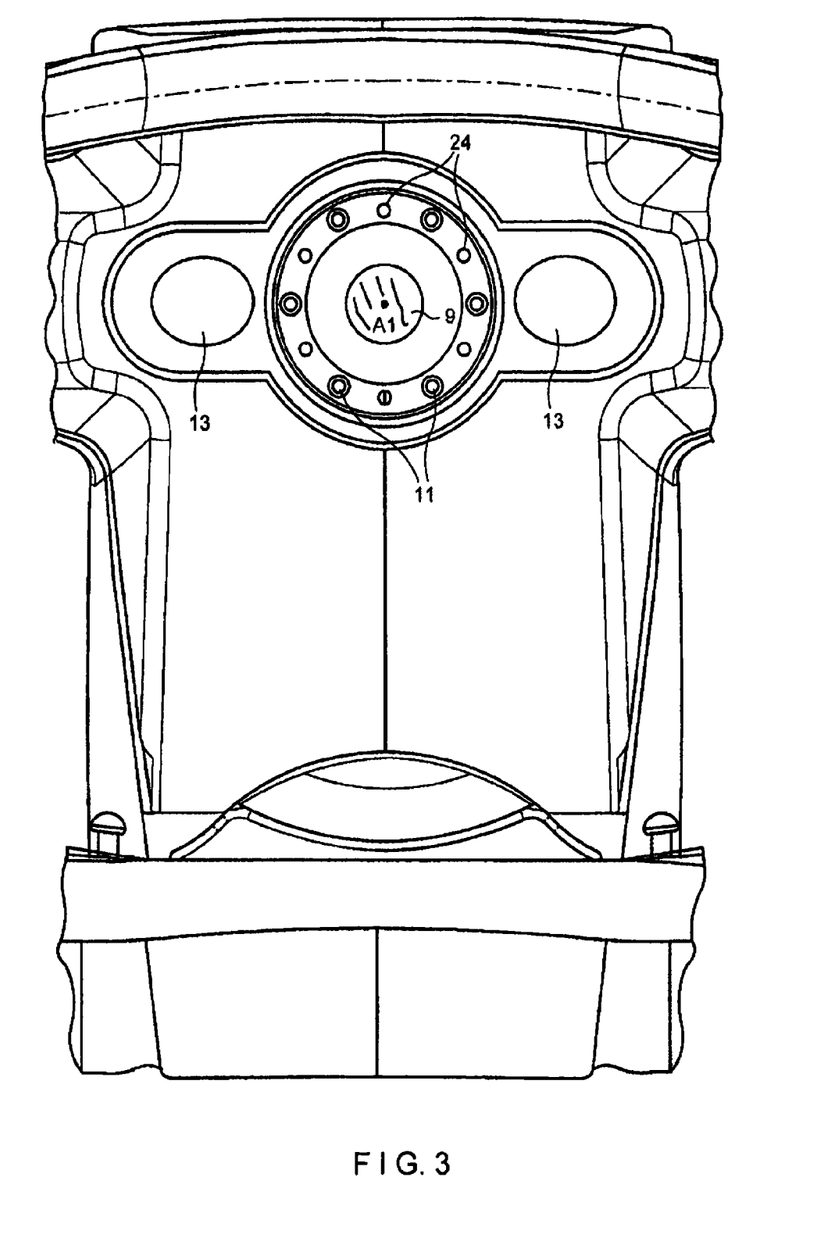
FIG. 3 shows a front view of the device in the direction of observation.

FIG. 3 shows a front view of the device in the direction of observation; a known slit lamp cross-slide stage for X-Y-Z adjustment is not shown.

The drawing shows the DOE 9 (whose center point A1 identifies the position of the optical axis in the device), lenses 11 for determining the corneal curvature and, located in back of the latter and not visible, LED 10, cylindrical lenses 13 for the slit imaging for measuring the VKT and six IR diodes 24 for illumination and alignment of the eye 14.

Figure 4:
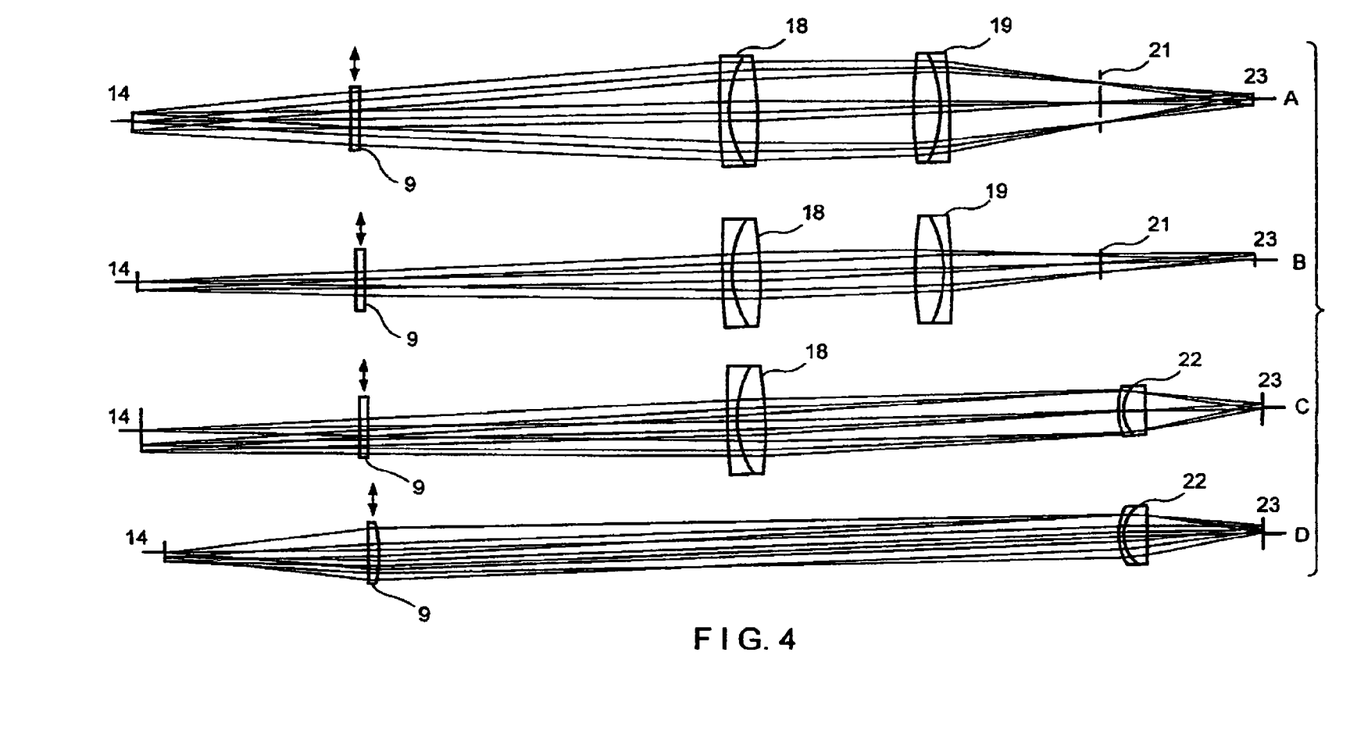
FIG. 4 shows the characteristic transmission path of the light in accordance with the invention.

The measurement tasks will be explained in more detail with reference to FIG. 4 based on the beam path A-D from the eye 14 to the CCD camera 23.

Beam Path C: Alignment of the Device Relative to the Eye

The eye lies within the focal length of the achromate 18, is imaged to infinity and is imaged, via achromate 22, in the plane of the CCD camera. Achromate 19 is swiveled out. The patient is asked to look at a fixating light using laser diode (LD) or LED 1 so that the patient orients the pupil in the direction of the optical axis. It is necessary to image a larger portion of the eye 14 (e.g., 15 mm) on the CCD camera. Due to its low efficiency (about 5% in the focusing part), the DOE is less suited for imaging the iris structures, so that an optical system with fixed image scale comprising achromates 18 and 22 carries out the imaging. The DOE is preferably swiveled out.

In order to avoid creating any additional fixation stimuli for the patient, the eye 14 is illuminated by means of IR diodes 24 (FIG. 2) (e.g., 880 mm) which are preferably characterized by a wide radiating characteristic (large half-power angle). The device is adjusted to the patient by means of the known slit lamp cross-slide table which is displaceable in the X-Y-Z directions. The CCD camera can be, for example, a VCM 3405 by Phillips. Illumination of the eye is necessary in order to be able to adjust the patient to the device also in darkened rooms. This illumination should be as diffuse as possible for a field of 15 mm; however, imaging of the light source through the cornea cannot be avoided (since the cornea acts as a convex mirror).

The basic idea in this case is to use the illuminating means for adjustment of the patient's eye at the same time.

Six infrared LEDs 24 with a relatively large half-power angle are arranged on the circumference of a circle (possibly the same circle circumference as in keratometer measurements). These LEDs 24 generate six points on the cornea which are imaged on the CCD camera. The eye of the patient is shown live on an LC display or monitor; in addition, a circle or cross-hair is shown on the LCD or monitor to mark the center. In order to position the eye, the six points must be centered with respect to the displayed circle. This is done by moving the cross-slide table. The patient is correctly adjusted with respect to height, side and depth when the points are centered and sharp. The patient himself looks into the device, from which an adjusting laser 1 or LED 1a is projected, and the patient must focus on the latter. The laser reflection is seen in the center of the pupil.

Additional adjusting means are to be shown on the LC display/monitor. An avalanche photodiode APD is provided for detecting the interference signals of the device measuring axial length.

When the patient's eye is on the optical axis of the measuring device, the adjusting laser 1 or LED 1a is reflected by the front surface of the cornea; the reflected light is imaged on the APD. In this way, a direct voltage signal whose (relative) height is a measure for the centering of the patient's eye is generated by the APD. This direct voltage signal is returned to the internal computer via an A-D converter and, from the latter, is displayed in appropriate form (e.g., a bar or circle) on the LCD. Accordingly, further information about the state of adjustment of the patient's eye is conveyed to the user through the varying size of the bar or circle.

Beam Path D: ALM

The reflections of the laser diode 1 (e.g., 780 mm) are imaged on the CCD camera 23 via the DOE, as parallel beam path, and the achromates 22, wherein an eye portion of about 5 mm with swiveled out optics 18, 19 is displayed for observation and reflection adjustment. In order to transmit maximum energy to the APD 17, a large part of the total energy on the APD, advantageously more than approximately 80 to 95%, is coupled out in the splitter cube 15 shown in FIG. 2; therefore, only approximately 20 to 5% of the light falls on the CCD camera.

Beam Path B: Keratometer

The illumination is preferably carried out in a manner analogous to DD 251497 by means of six IR diodes 10 (e.g., 880 nm) in order not to inhibit the fixation of the patient's eye 14 on the fixating light of the LD 1 or LED 1a.

The predetermined resolution of the CCD camera 23 requires the imaging of a field no larger than approximately 6 mm on the eye 14 in order to achieve a measurement accuracy of 0.05 mm. The action of the DOE is preferably canceled again by swiveling it out and the achromates 18 and 19 carry out the imaging of the six cornea reflection images.

The following are used to increase a measuring accuracy which is extensively independent from the distance from the patient's eye to the device:

a telecentric diaphragm 21 which preferably limits the aperture for measurement to less than 0.05; and collimators 11 which are located between the LED and the patient's eye and which keep the incident angle constant independent from the axial position of the patient's eye.

The imaging of the LED light is advantageously carried out via a pinhole diaphragm 10a which enables exact alignment of the keratometer measurement points. The collimator focal length should be greater than fifty-times the effective light source extension in order to achieve the desired accuracy of radial measurement independent from position.

Beam Path A: VKT

Due to the fact that light scattering is the decisive factor in the observation of light sections in the human eye, a light source with the shortest possible wavelength (e.g., 400-600 nm) must be selected for illumination of the eye 14. Also, in determining the VKT, a field no greater than approximately 6 mm at the eye 14 may be imaged on the CCD camera 23 to achieve the required measuring accuracy of 0.1 mm. This is accomplished by means of the achromates 18 and 19 while circumventing the DOE effect or when the DOE is swiveled out. Achromate 22 is swiveled out. The telecentric diaphragm 21 which is swiveled in or adjusted must have a greater diameter (for an aperture which is preferably greater than 0.07, e.g., 13 mm) in order that the light intensity of the low-light scatter images occurring in the VKT measurement is reduced only minimally. Accordingly, it is adjustable in at least two positions or can be exchanged for a second diaphragm.

The eye of the test subject is illuminated from the side at a fixed angle through the bright light slit. The light sections occurring on the eye are imaged on the CCD camera by an optical system 18, 19, 21. Illumination and observation form a fixed angle, preferably approximately 33.degree.

Figure 8A:
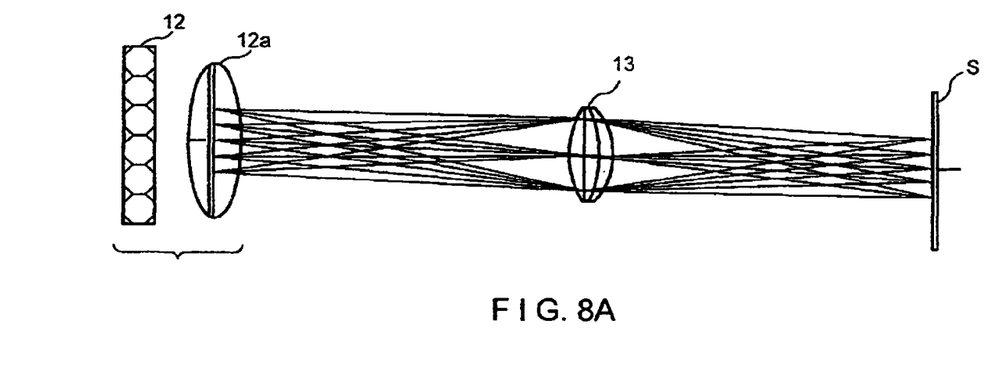
FIGS. 8a and 8b show further illustrations of the optical paths in accordance with the invention.
Figure 8B:
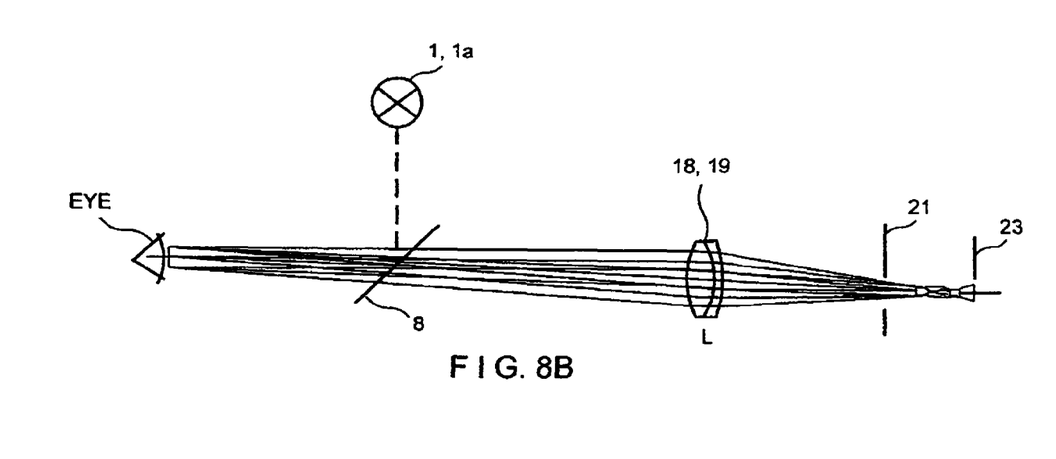

FIG. 8*a, b* is a schematic view of the arrangement for determining the VKT in the illumination direction in FIG. 8*a* and in the detection direction in FIG. 8*b*.

The light slit is formed by a line of light-intensive LEDs 12 which are at a defined distance from a slit 12*a* of fixed width.

The slit 12*a* which is illuminated in this manner is imaged on the test subjects eye through a cylindrical lens 13 as slit image S.

The utilized LEDs typically last at least 10,000 hours (compared to 100-200 hours in halogen lamps).

There are no wear phenomena due to temperature load as in halogen lamps.

Imaging of the eye of the test subject is preferably carried out with the relevant image sections via imaging optics 18, 19, shown schematically, preferably on a CCD sensor 23. The imaging is carried out telecentrically—telecentric diaphragm 21—in order to minimize the influence of the alignment of the test subject. The video signal is displayed on a monitor or LC display, so that the user can carry out the adjustment of the test subject and the measurement in a natural posture.

The measurement process is not based on the measurable displacement of partial images; therefore, the pupil division can be dispensed with.

The signal of the CCD camera 23 is received in the memory of the computer C by means of a frame grabber FG.

Suitable image processing software is used for determining distances in the section image from which the VKT (accuracy 0.1 mm) is calculated.

An improvement in the relevant image contents (e.g., by eliminating ambient light) is achieved in that the illumination LEDs in suitable form are turned on and off cyclically synchronous to the video fields.

An achromate having a defined focal length is sufficient for imaging the eye on the CCD camera. The focal length is determined depending on the desired image section at the eye to be imaged.

The diaphragm 23 satisfying the condition of telecentrism is arranged in the image-side focal length of the achromate.

This simple construction of the imaging system ensures the possibility of uncomplicated integration in other systems.

The fixating light 1, 1*a* (LED) is blended in via beam splitter 8 in FIG. 8*b*.

A light source (e.g., LED 1*a* or laser diode 1) on which the subject fixes his gaze is integrated in the observation system.

The video signal of the camera is displayed on a monitor or LC display.

The user can confirm during adjustment and measurement of the subject that the subject's gaze is correctly fixed and, therefore, that the measurement results are not corrupt.

The slit which is illuminated in this manner is imaged on the test subject's eye (4) through a cylindrical lens.

Imaging—diverging slightly from a 1:1 imaging—of a slit with a width of 0.3 mm and aperture greater than 0.1 and the use of white-light LEDs have proven particularly advantageous.

Imaging of the eye of the test subject is preferably carried out with the relevant image sections via imaging optics 18, 19, preferably on a CCD sensor 8. The imaging is carried out telecentrically in order to minimize the influence of the alignment of the test subject. The video signal is displayed on a monitor or LC display, so that the user can carry out the adjustment of the test subject and the measurement in a natural posture.

The signal of the CCD camera is sent to the memory of a computer, e.g., by means of a frame grabber. Suitable image processing software is used for determining distances in the section image from which the VKT (accuracy 0.1 mm) is calculated. An improvement in the relevant image contents (e.g., by eliminating ambient light) is achieved in that the illumination LEDs in suitable form are turned on and off cyclically synchronous to the video fields.

In the following, it will be shown with reference to FIG. 7 how the VKT is determined based on the image on the CCD matrix. The Figure shows the image of the eye that is detected by the CCD camera with the reflection image FI of the adjusting laser and fixating LEDs, and the scatter light SH of the cornea and lens SL with illumination 1 switched on.

Determination of the Distance of the Front Edges of the Scatter Images of the Cornea and Lens in Digitized Recordings The starting point for image processing is (n times) a pair of images recorded in immediate succession: image 1 with switched on slit illumination ("bright image") and image 2, without slit illumination, with image of the fixating lamp ("dark image"). Processing is carried out through the following essential steps:

detection of the pupil in the dark image: histogram-based selection of a threshold value for binarization taking into account boundary constraints; determination of an ellipse circumscribing the pupil by evaluating the covariance matrix of the binary image;

detection of the fixation point in the pupil in the dark image: determination of all contiguous regions whose gray values are above the 0.9-quantile of the gray value distribution in the dark image; determination of a probability quantity for every region which depends on surface, shape and distance from the center point of the pupil; selection of the centroid of the likeliest region as fixating point;

calculation of the differential image (bright image minus dark image) and noise suppression in the differential image by means of median filtering;

determination of the edge shape of the scatter images of the slit illumination in the differential image: histogram-based selection of a threshold value for binarization taking into account boundary constraints; rough determination of the edges as location where threshold value is exceeded in given region around the fixating point; fine-tuned detection of the edges as location of the reversal point of the gray value shape in the line profile which comes closest to the roughly detected position; elimination of reflection edges by detection of mavericks or freak values in the edge shape (distance of a given proportion of points furthest from the average edge shape);

determination of the distance X of the front edges of cornea scatter image and lens scatter image SH, SL (in pixels): approximation of the edge shape through ellipses (restricted minimization of the square error sum); calculation of the distance of the intersections of these ellipses with the horizontal through the fixating point.

Calculation of the Anterior Chamber Depth from the Above-Mentioned Distance:

Conversion of the distance K in pixels into mm (including imaging scale of optics and pixel size of CCD matrix)
r=corneal radius
n=index of refraction of the aqueous humor
omega.=angle between illumination and observation $$VKT = r + \frac{x}{\tan\left[\arcsin\frac{\sin\left(\omega - \arcsin\frac{x}{r}\right)}{n} + \arcsin\frac{x}{r}\right]} - \sqrt{\left\{\frac{x}{\tan\left[\arcsin\frac{\sin\left(\omega - \arcsin\frac{x}{r}\right)}{n} + \arcsin\frac{x}{r}\right]}\right\}^2 - \left\{\frac{x}{\sin\left[\arcsin\frac{\sin\left(\omega - \arcsin\frac{x}{r}\right)}{n} + \arcsin\frac{x}{r}\right]}\right\}^2 + r^2}$$

Figure 7:
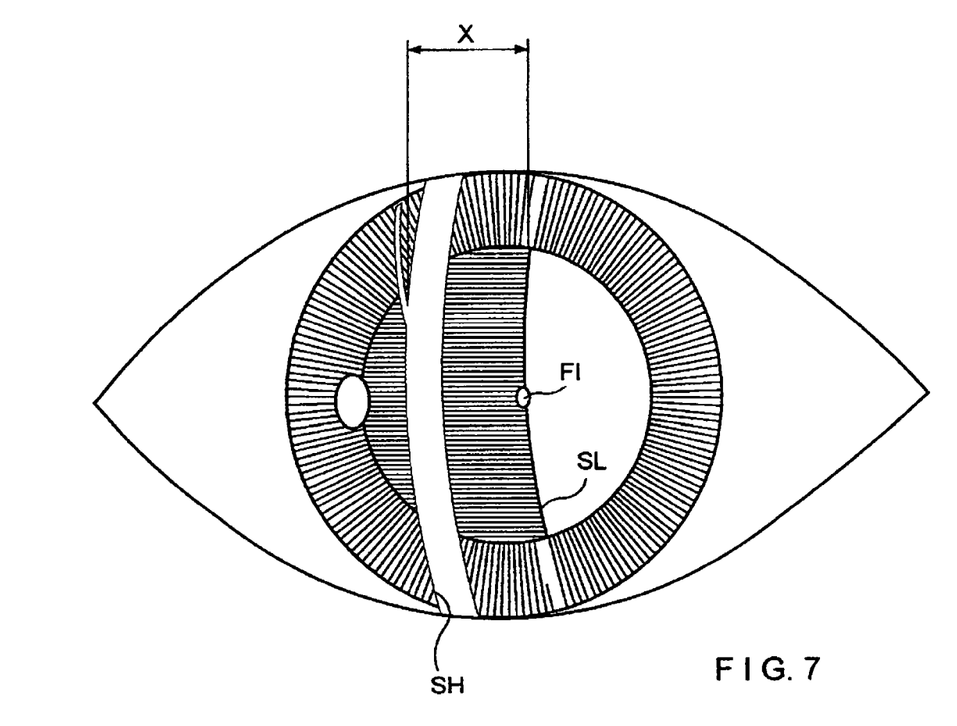
FIG. 7 shows how the VKT is determined based on the image on the CCD matrix.

This formula applies exactly when the image of the fixating lamp is located at the front edge of the lens scatter image as is shown in FIG. 7; otherwise, the distance of the fixating lamp image from the front edge of the lens scatter image can be determined and a correction value can be determined for the anterior chamber depth from the amount of this "decentering" based on known imaging formulas. The corneal radius is preferably measured by means of the keratometer device described above.

Following is an overview of characteristic settings to be considered when combining the three required measurements and the adjusting process:

|  | Adjustment | ALM | Keratometer | VKT |
|---|---|---|---|---|
| Field size | approx. 15 mm | approx. 5 mm | approx. 6 mm | approx. 6 mm |
| Wavelength | IR (e.g., 880 nm) | e.g., approx. 780 mm | IR (e.g., 880 nm) | VIS (e.g., 400-600 nm) |
| Beam diaphragm | removed | removed | approx. 6 mm | approx. 13 mm |
| DOE | no effect (removed) | active | no effect (removed) | no effect (removed) |

As this overview shows, different wavelength ranges are used with the different measurement tasks. The splitter cubes 8 and 15 are very important in this connection, since the illumination beam path, observation beam path and measurement beam path are separate from one another. This task is performed by special splitter layers taking into account the linear polarization of the laser diode 1.

Splitter Cube 8:

The laser light coming from the interferometer should be reflected at a maximum in the direction of the eye 14; the laser light coming from the eye 14 should have maximum transmission. In addition, the splitter layer in the cube 8 must have maximum transmission for the IR light component and VIS light component of the keratometer measurement and VKT measurement. Since the LD 1 (for example, LT 023, Sharp) involves linearly polarized light, a dielectric multiple layer with a polarizing effect can preferably be used. The characteristic transmission path is shown in FIG. 4. The vertically polarized light (s-pol, 780 nm) coming from 1 is reflected as much as possible (approximately 98%).

Figure 6A:
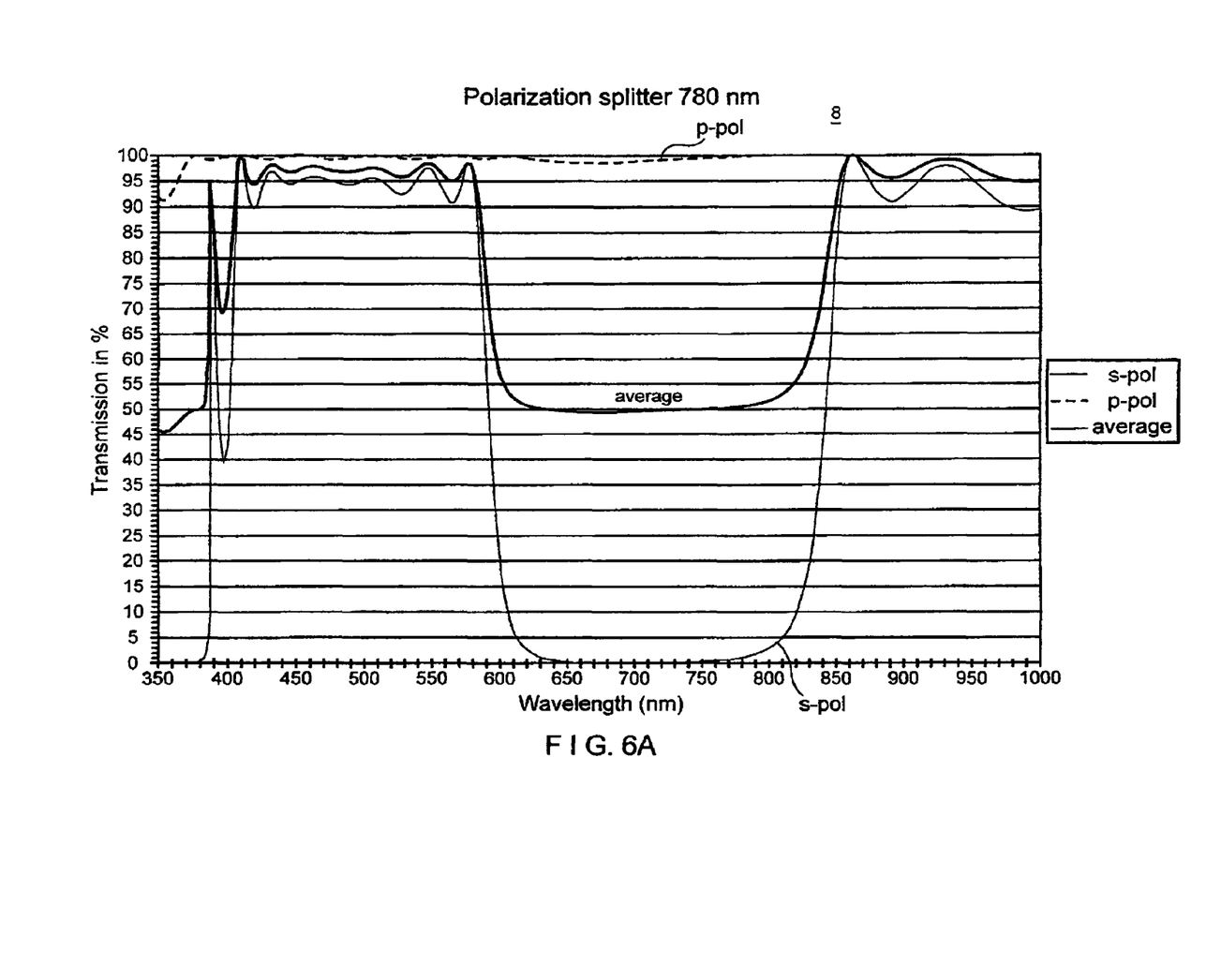
FIG. 6a shows the transmission of the polarization splitter.

Circularly polarized light is generated by the quarter-wave plate. The light reflected by the eye 14 is accordingly linearly polarized again after passing the quarter-wave plate; however, the polarization direction is rotated by 90.degree. (parallel-polarized, p-pol). For this oscillation direction, the splitter layer has approximately 100% transmission at 780 nm. The IR and VIS LEDs emit unpolarized light. As will be gathered from FIG. 6, the transmission of the splitter layer in the wavelength range of 420 to 580 nm and in the range of 870 to 1000 nm is greater than 90% for unpolarized light.

Construction of Layer: Splitter Cube 8:

Aside from its normal function—high polarization splitter effect in a defined wavelength range—this polarization splitter cube fulfills additional requirements of high transmission in the visual wavelength range (420 . . . 560 nm) and in the near infrared range (870 . . . 1000 nm). The layer design meets these requirements for a narrow incident angle range of 46.degree.. The utilized materials are adapted to one another with respect to the refractive index of the substrate, cement and coating substances. The following materials were selected for this special use:

| Substrate: | SF2 | n = 1.64 |
|---|---|---|
|  | cement | n = 1.64 |
|  | H | n = 1.93 |
|  | L | n = 1.48 |

The design is formed of 17 alternating layers of H L. HFO2 is H, SI02 is L.

For comparable splitters, suitable splitters can be fabricated by suitable selection of the index of refraction of the substrate and coating substances and angle of incidence.

Parameters:
high transmission of 420 . . . 560 nm, unpolarized
high transmission of 870 . . . 1000 nm, unpolarized
polarization splitting 780.+−.20 nm Example

| 1 | HFO2 156.8 nm |
|---|---|
| 2 | SIO2 118.1 nm |
| 3 | HFO2 166.4 nm |
| 4 | SIO2 95.8 nm |
| 5 | HFO2 160.2 nm |
| 6 | SIO2 147.3 nm |
| 7 | HFO2 145.6 nm |
| 8 | SIO2 151.0 nm |
| 9 | HFO2 144.9 nm |
| 10 | SIO2 148.2 nm |
| 11 | HFO2 149.2 nm |
| 12 | SIO2 139.9 nm |
| 13 | HFO2 161.3 nm |
| 14 | SIO2 103.9 nm |
| 15 | HFO2 179.5 nm |
| 16 | SIO2 64.9 nm |
| 17 | HFO2 170.9 nm |

Splitter Cube 15:

The laser light coming from the splitter cube 8 should be reflected by about 80 to 95% with a transmission of approximately 20-5%, The splitter layer should have maximum transmission for the IR and VIS light components. This layer is likewise realized by a polarization splitter which resembles the splitter layer in 8 with respect to its characteristics. The half-wave plate arranged on the splitter cube 15 rotates the polarization direction of the arriving light by 90.degree so that the s-pol component again impinges on splitter cube 15. The splitter ratio mentioned above is adjusted by modifying the layer 8. For unpolarized light in the IR and VIS range, the transmission is greater than 90%.

Figure 6B:
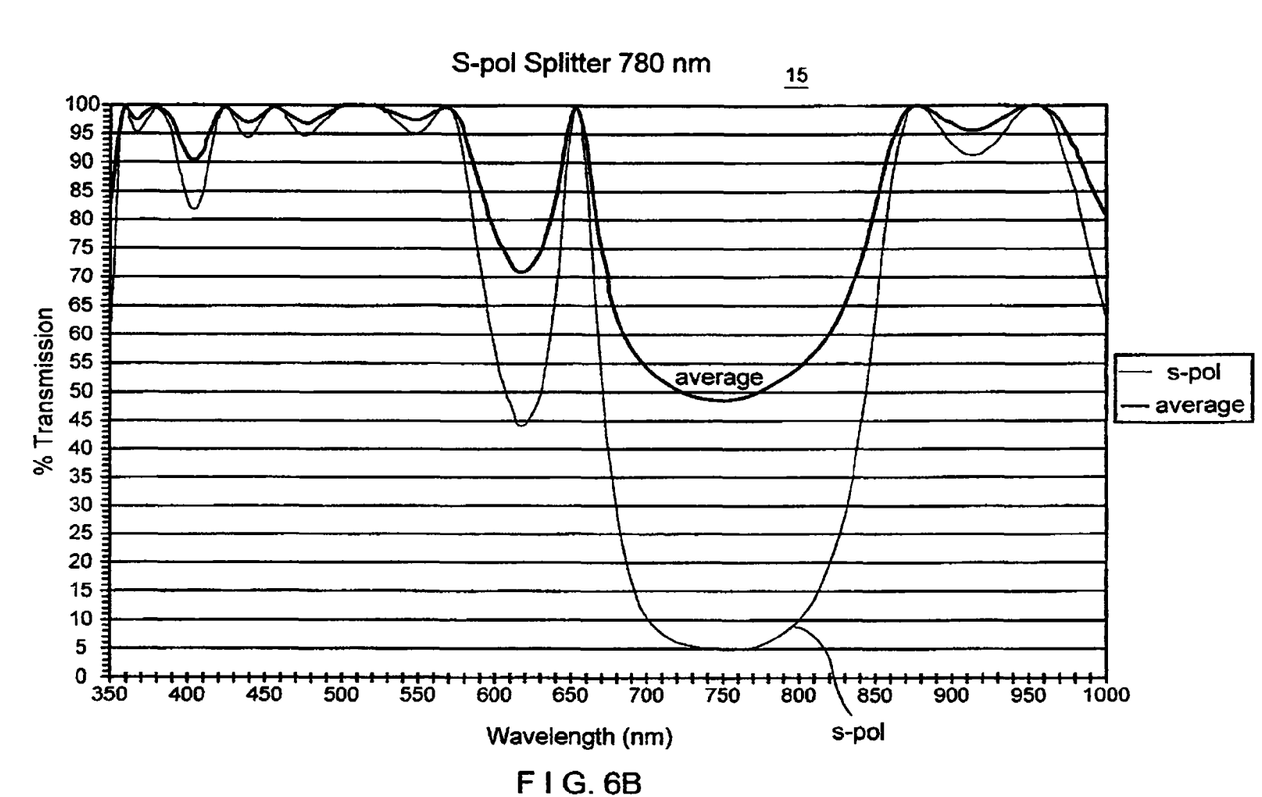
FIG. 6b shows the transmission of the S-pol splitter.

Construction of the Layer: Splitter 15:

Apart from the requirements of the s-pol reflection of 80 . . . 95% with a wavelength of 780 nm.+−.20 nm, the splitter cube meets the additional requirements of high transmission in the visual wavelength range (420 . . . 560 nm) and in the near infrared range (870 . . . 1000 nm) (FIG. 6b). The layer design satisfies these requirements for a narrow incident angle range of 46.degree.. The utilized materials are adapted to one another with respect to the refractive index of the substrate, cement and coating substances. The following materials were selected for this special use:

| Substrate: | BK7 | n = 1.52 |
|---|---|---|
| | cement | n = 1.52 |
| | H | n = 1.93 |
| | L | n = 1.48 |

The design is formed of 13 alternating layers of H L.

For comparable splitters, suitable splitters can be manufactured by suitable selection of the index of refraction of the substrate and coating substances and angle of incidence.

Parameters:
high transmission of 420 . . . 560 nm, unpolarized
high transmission of 870 . . . 1000 nm, unpolarized
reflection s-pol approximately 80 . . . 0.95% 780.+−.20 nm Example

| 1 | HFO2 130.2 nm |
|---|---|
| 2 | SIO2 215.4 nm |
| 3 | HFO2 130.6 nm |
| 4 | SIO2 17.8 nm |
| 5 | HFO2 160.7 nm |
| 6 | SIO2 241.6 nm |
| 7 | HFO2 136.6 nm |
| 8 | SIO2 240.0 nm |
| 9 | HFO2 156.4 nm |
| 10 | SIO2 18.0 nm |
| 11 | HFO2 135.1 nm |
| 12 | SIO2 214.1 nm |
| 13 | HFO2 131.3 nm |

Figure 5:
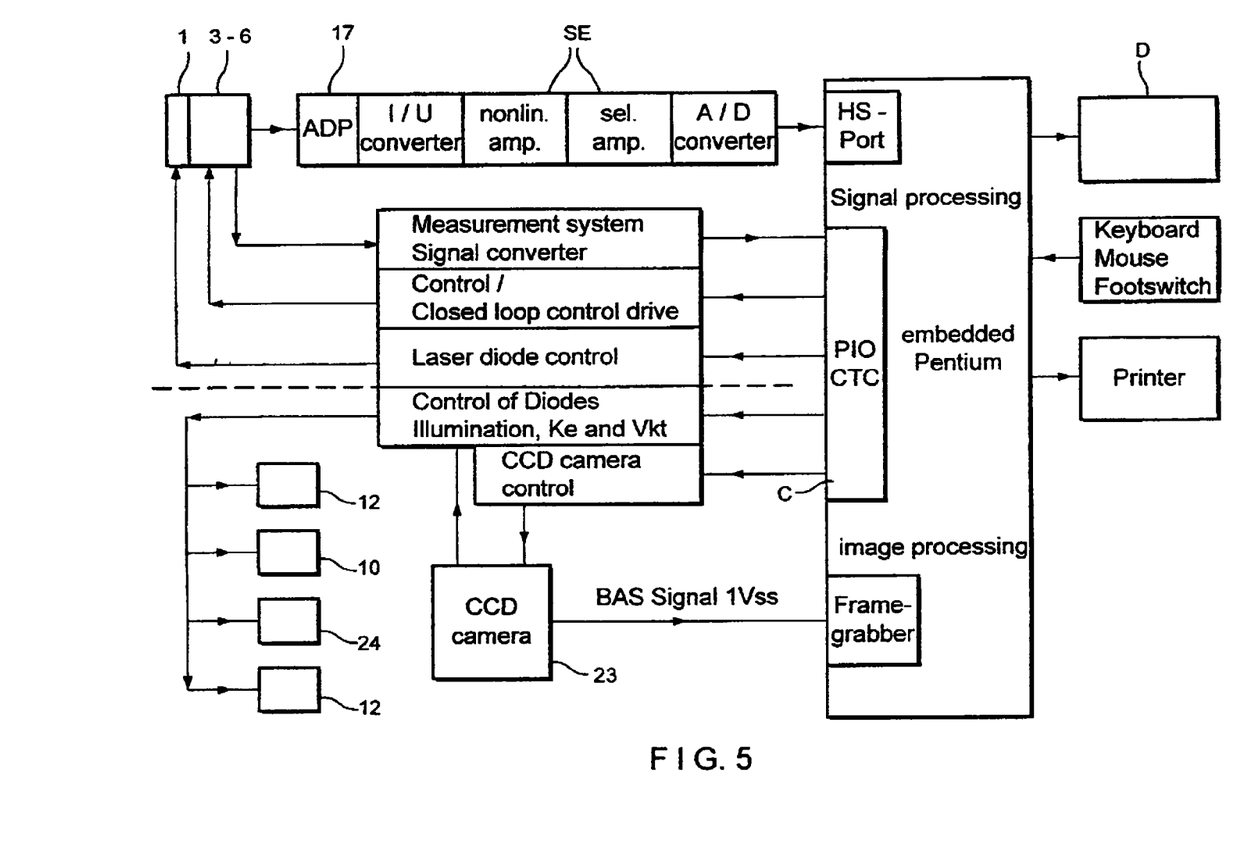
FIG. 5 is a block diagram showing central control of the system in accordance with the invention.

According to FIG. 5, a central control is provided for adjusting and controlling all adjustable units and optical elements such as optics 18, 19, 22, diaphragm 21, etc.

The different imaging scales taking into account the action of the DOE call for reversing processes in the device. These reversing processes are preferably carried out by means of motor and in a program-controlled manner.

A compact device has been realized in which the essential electronics building blocks are integrated. The heart of the device is an embedded Pentium controller C to which are connected a display D (showing the eye 14 being examined and a menu for the user), keypad, mouse, foot switch and printer as peripheral equipment.

ALM

The control of the laser diode 1 and interferometer slide IS (movable prism 5, connected with measuring system) is carried out via the controller C. To reduce the influence of eye movements, a short measuring time (less than 0.5 sec) must be realized. The signal generated by the APD 17 reaches a signal processing unit SE, is amplified depending on the signal size, then amplified in a frequency-selective manner and converted from analog to digital at a sampling frequency corresponding to approximately four-times the frequency of the useful signal. The digital sampling values are taken over by the high-speed port HS of the Pentium platform. Digital signal processing is carried out in the latter by means of Fourier transformation without externally generated reference frequency. The signal is shown on the display; the path measurement system delivers the respective axial length quantity.

Keratometer

The controller C is connected with the control of the CCD camera 23 and the diodes 10. In the adjusting process for measuring the corneal curvature, the diodes 10 are preferably operated in continuous light mode in order to prevent flickering of the corneal reflected images shown on the LCD. During the measuring process, these diodes are switched on and off imagewise; for this purpose, the controller C controls the diodes 10 synchronously with the image pulse of the CCD camera 23, i.e., the diodes are switched on in one image and switched off in the next image. After subtraction of two successive images, only the reflections of the cornea that were generated by the LEDs 10 are obtained in image pairs, and interfering reflections of ambient light are eliminated. The reflection images occurring on the camera 23 are digitized by means of frame grabbers FG and are stored in the working memory of the Pentium platform (controller C).

Subsequently, the centroid positions of the reflection images of the diodes are determined by means of image processing and calculation of the corneal radii by means of the approximation formulas described in DD 251497. To improve the reproducibility of the measurement results, approximately 5 image series (each comprising two fields or half-images, with and without exposure by the synchronized LEDs) are recorded per measurement process.

VKT

Further, the controller C is connected with the diodes 12. During the adjusting process (alignment), the diodes 12 are preferably operated in continuous light mode in a manner analogous to the keratometer.

During the measuring process, the illumination diodes for the left and right eye are selectively cycled (similar to the keratometer) by the controller.

Depending on the user preset, the device is displaced to the left or to the right and is aligned with the center of the eye by appropriate means.

The edge position of the scatter images is determined by means of image processing.

The VKT is calculated from the distance of the cornea and lens scatter images as was already described. Again, approximately 5 image series are recorded per measurement process.

Illumination

The controller C is connected with the diodes 24. The IR diodes 24 for illuminating the eye can be switched on at a desired time by means of the controller (so as to be controlled within the program or by the user). Further, the controller is connected (not shown) with the controls for swiveling in and swiveling out or adjusting the DOE 9, lenses 18, 19, 22 and diaphragms 21.

The calculation of the IOL from the determined measurement values AL, HEIR, VKT is carried out by means of internationally recognized calculation formulas which are stored in the device memory so as to be retrievable and is printed out by the printer.

While the foregoing description and drawings represent the present invention, it will be obvious to those skilled in the art that various changes may be made therein without departing from the true spirit and scope of the present invention.

The invention claimed is:

1. An apparatus for non-contacting measurement of axial length and anterior chamber depth of an eye, the apparatus comprising:
   an interferometer device for measuring the axial length of the eye, wherein the interferometer device comprises at least one adjustable element for adjusting a path length difference and a detector for detecting interfering radiation,
   a light path having a source of slit-shaped illumination radiated on the eye at a non-zero angle to an observation axis measured at the eye, and the light path comprising slit imaging optics and at least one light source;
   a receiver separate from the detector which detects scatter images coming from structures of the eye and which is located substantially on the observation axis, the receiver, the slit shaped illumination and the imaging optics being angularly fixed relative to each other; and
   a signal processing device which controls the interferometer device, receives signals from the detector and calculates the axial length and which receives signals from the receiver and processes the signals to determine distances between portions of the scatter images that represent the structures of the eye and calculates anterior chamber depth from the distances.

2. The apparatus according to claim 1, wherein an angle between the observation axis and the axis upon which the slit-shaped source of illumination radiates on the eye is fixed.

3. The apparatus according to claim 2, wherein the angle between the observation axis and the axis upon which the source of slit-shaped illumination radiates on the eye is about 33 degrees.

4. The apparatus according to claim 1, wherein the source of illumination comprises a slit arranged after the at least one light source in the illumination direction.

5. The apparatus according to claim 1, wherein the imaging optics are constructed anamorphotically or include a cylindrical lens.

6. The apparatus according to claim 1, wherein the receiver comprises a CCD camera.

7. The apparatus according to claim 1, in which the source of slit-shaped illumination comprises a series of white light LEDs.

8. The apparatus of claim 1, wherein the interferometer device for measuring the axial length of the eye comprises two arms with the adjustable element being provided in one of the two arms.

9. The apparatus according to claim 1, which is further adapted for measuring corneal curvature or corneal radius of curvature of the eye and comprises:
   a ring of light sources illuminating the cornea with a ring-type illumination and a camera for detecting reflection of the ring-type illumination,
   wherein the signal processing device also receives signals from the camera and calculates the corneal curvature or corneal radius of curvature of the eye.

10. The apparatus according to claim 9, wherein the illumination sources of the ring of illumination sources are LEDs.

11. The apparatus according to claim 9, comprising a beam splitter splitting radiation coming from the eye into a beam path to the detector of the interferometer device and a beam path to the camera detecting reflection of the ring-type illumination.

12. The apparatus according to claim 1, further comprising a fixating light source emitting a fixating light on which the patient fixes his gaze, the fixating light being radiated along an optical axis, to align the patient's viewing axis along the optical axis.

13. The apparatus according to claim 1, wherein the at least one light source comprises an LED.

14. The apparatus according to claim 4, wherein the at least one light source comprises an LED.

15. The apparatus according to claim 1, wherein the adjustable element for adjusting a path length difference comprises a reflector.

\* \* \* \* \*